United States Patent [19]
Wachter et al.

[11] Patent Number: 5,483,338
[45] Date of Patent: Jan. 9, 1996

[54] METHOD AND APPARATUS FOR EVALUATING STRUCTURAL WEAKNESS IN POLYMER MATRIX COMPOSITES

[75] Inventors: Eric A. Wachter, Oak Ridge; Walter G. Fisher, Knoxville, both of Tenn.

[73] Assignee: Martin Marietta Energy Systems, Inc., Oak Ridge, Tenn.

[21] Appl. No.: 248,802

[22] Filed: May 26, 1994

[51] Int. Cl.[6] .......................... G01N 21/64; G01N 21/88
[52] U.S. Cl. .................. 356/318; 356/417; 250/458.1
[58] Field of Search ................................ 356/317, 318, 356/417, 237; 250/458.1, 459.1, 461.1

[56] References Cited

PUBLICATIONS

C. J. Janke et al, "Composite Heat Damage Spectroscopic Analysis," ORNL/ATD–42, Sep. 1990.
G. L. Powell et al, "Nondestructive Inspection of Graphite–Epoxy Laminates for Heat Damage Using DRIFT and LPF Spectroscopies," Y/DZ–1008/R1 (Preprint), Jun. 3, 1993.

*Primary Examiner*—F. L. Evans
*Attorney, Agent, or Firm*—W. Allen Marcontell; Shelley L. Stafford; Harold W. Adams

[57] ABSTRACT

A method and apparatus for evaluating structural weaknesses in polymer matrix composites is described. An object to be studied is illuminated with laser radiation and fluorescence emanating therefrom is collected and filtered. The fluorescence is then imaged and the image is studied to determine fluorescence intensity over the surface of the object being studied and the wavelength of maximum fluorescent intensity. Such images provide a map of the structural integrity of the part being studied and weaknesses, particularly weaknesses created by exposure of the object to heat, are readily visible in the image.

12 Claims, 3 Drawing Sheets

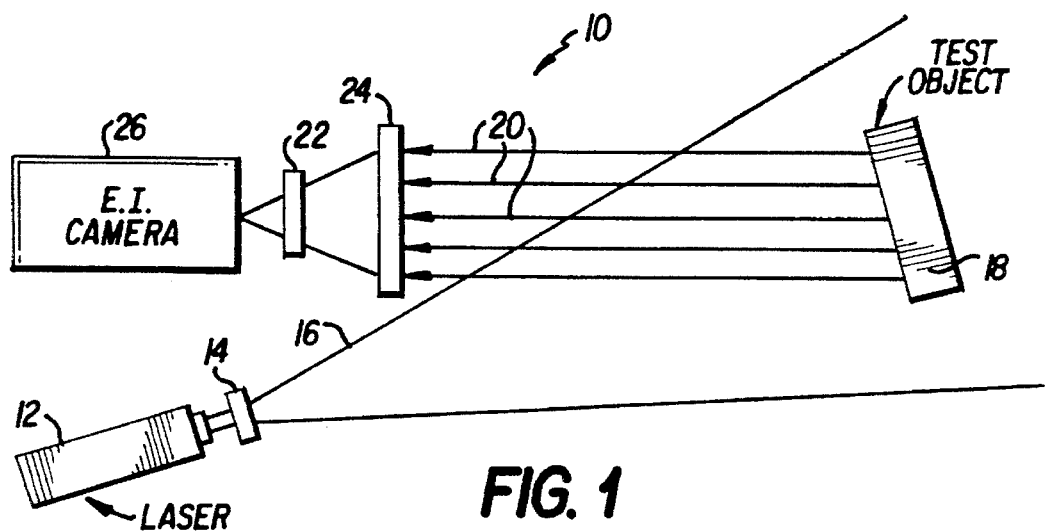
FIG. 1
FIG. 2
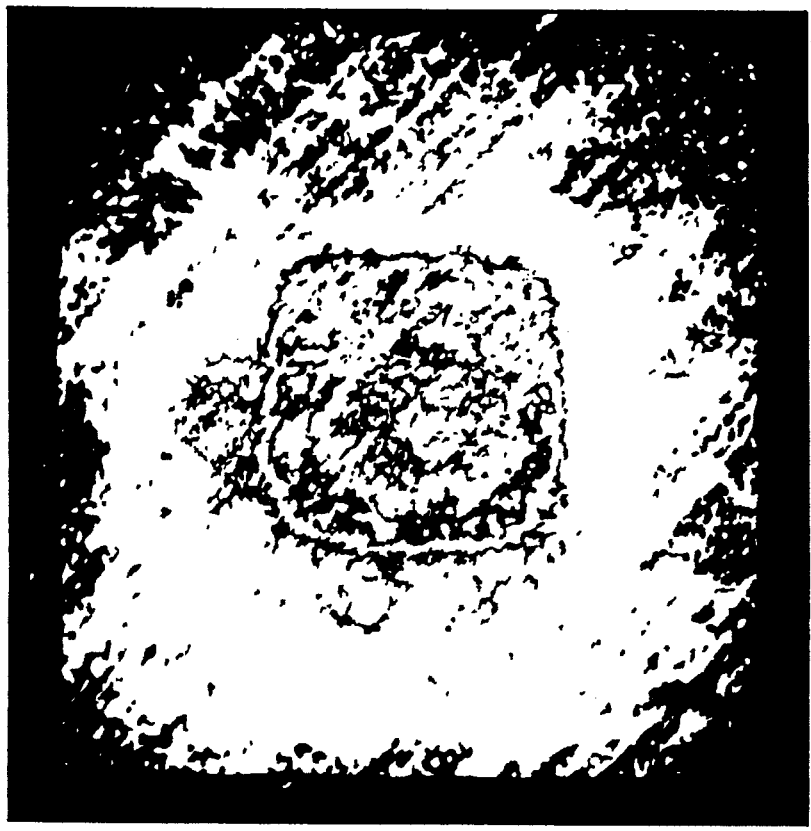

METHOD AND APPARATUS FOR EVALUATING STRUCTURAL WEAKNESS IN POLYMER MATRIX COMPOSITES

This invention was made with Government support under Contract No. DE-AC05-840R21400 awarded by the U.S. Department of Energy to Martin Marietta Energy Systems, Inc. and the Government has certain rights to this invention.

FIELD OF THE INVENTION

This invention relates to the field of evaluating heat damage in materials and, particularly, to evaluating heat damage in items formed of polymer matrix composites.

BACKGROUND OF THE INVENTION

Polymer-Matrix Composites (PMC's) are extremely useful for many applications due to their high performance, strength and stiffness combined with their low weight and resistance to corrosion. However, despite the benefits of PMC's, they are very sensitive to elevated temperatures. Even brief exposure to elevated temperature can result in significant irreversible degradation of key physical properties of such fiber-reinforced PMC's which are commonly used.

Apparently, a key mechanism in heat-related damage of PMC's is chemical rather than physical degradation of the resin component of the composite. Thus, significant losses of strength, on the order of 10–50%, can occur with no macroscopic indicators such as internal or surface delamination, cracking, swelling or color change. Since there are no macroscopic indicators, it is impossible to detect such changes using traditional techniques such a x-ray imaging or ultrasound, which function to image macroscopic or microscopic physical features. The physical features which would represent a loss of structural integrity in other commonly used construction material are simply not present; except in severely damaged PMC parts.

However, due to the characteristics of non-damaged PMC's, their use where exceptional strength and lightness are required is rapidly expanding. PMC's are used in critical structural components for the aerospace industry, weapons manufacturing, transportation, construction and a variety of other fields. In these areas, even a minor degradation of structural strength is a serious concern as the safety of large numbers of people and very expensive machinery depends on the structural members used. Additionally, since many PMC items are made as large pieces, they can be very difficult and expensive to examine with techniques associated with the examination of smaller parts or samples of parts.

Further, although relatively expensive and difficult imaging techniques may be utilized to detect some of the damage in PMC's, such techniques are limited to large companies in limited applications due to their prohibitive cost. These techniques are only employed in industries such as the aerospace industry where the potential liability for the failure of a damaged PMC structural member can be astronomical. Smaller companies making less critical uses of PMC's cannot afford the high cost of presently available non-destructive testing techniques, since the costs are not offset by a corresponding risk. Analysis of PMC components for items such as oars, bicycles, kayaks, canoes, surf boards, etc. must be relatively simple and inexpensive before such analysis will be routinely used for quality control/quality assurance programs in these fields.

It is therefore an object of the present invention to provide a method for the optical identification of heat damage in PMC parts.

It is a further object of the present invention to provide a low cost method for optically detecting heat damage in PMC's.

It is yet a further object of the present invention to provide a method for imaging damage in PMC's which allows for the rapid evaluation of large parts.

It is a further object of the present invention to provide a high speed method for imaging damage in PMC's.

it is still a further object of the present invention to provide an apparatus for the evaluation of heat damage in PMC parts utilizing Laser Induced Fluorescence (LIF).

SUMMARY OF THE INVENTION

The above and further objects are realized in a method and apparatus for imaging heat damage in polymer-matrix composites (PMC's) made in accordance with the preferred embodiment of the present invention. In a preferred embodiment, a method for imaging PMC's provides a means to detect heat damage in parts made therefrom. In a preferred embodiment, a laser beam of desired wavelength is spread to effectively illuminate a substantial portion of the object to be studied. As the object is illuminated, it will fluoresce and such fluorescence is collected, filtered to remove elastically scattered laser radiation and imaged. The image is analyzed to determine peak fluorescence intensity and wavelength of peak intensity to determine areas of structural weakness.

In an alternate embodiment, the object is illuminated as was previously described. Once again, the fluorescence is collected and elastically scattered laser radiation is filtered from the collected fluorescence. A bandpass filter is interposed into the collected and filtered fluorescence to allow the imaging of a selected narrow wavelength band. The intensity of a selected number of discrete points in the image is determined in a series of similar images that are produced for a preselected number of wavelength bands. This procedure results in the generation of an array of laser induced fluorescence images of the object at discrete wavelength bands. The array is analyzed to determine the wavelength of maximum intensity of the fluorescence for a number of discrete points in the images and an image of wavelength of maximum fluorescent intensity is generated therefrom. This image may then be analyzed to determine areas of structural weakness within the object being observed.

In a further embodiment, an apparatus for generating images showing structural weakness in PMC's is provided. A laser generates a laser beam which is provided through a spreading lens. The spread beam is then used to illuminate a substantial portion of an object to be studied. Laser induced fluorescence from the object is collected using a collection lens or mirror and directed through a long pass filter which filters any elastically scattered laser radiation from the collected fluorescence. The collected fluorescence is then provided to a charged coupled device (CCD) camera to image the fluorescence emitted by the object. The image generated by the CCD camera provides an image of fluorescence intensity over the illuminated portion of the object which will reveal structural weaknesses in the object.

In an alternate embodiment, a laser and spreading lens is once again provided to illuminate an object with laser radiation. Similarly, a collection lens or mirror is utilized to collect fluorescence emitted by the object and provided to a long pass filter which filters in the elastically scattered laser radiation. The collected fluorescence is then provided to a tunable bandpass filter which selectively transmits relatively narrow wavelength bands into a CCD camera for imaging. A number of images are made at a variety of wavelength bands generating a number of images of laser induced fluorescent intensity at each of the wavelength bands. The array of images is analyzed at a number of discrete points common to each of the images and the wavelength of maximum fluorescence intensity is determined for each of the discrete points. A composite image is then generated based upon the wavelength of maximum intensity at each of the discrete points which provides an image of the object showing the wavelength of maximum intensity for each of the discrete points which reveals structural weaknesses in the object.

In an alternate embodiment, the tunable bandpass filter and CCD camera are connected to a computer. The computer automatically controls the bandpass filter in accordance with programmed wavelength bands to be studied. The output of the CCD camera is provided to the computer which then performs the analyses on the array of fluorescence intensity images at the selected wavelength bands. The computer then generates the composite image of the wavelength of maximum fluorescent intensity at each of the discrete points studied. The image may then be further enhanced by the computer to generate a false color representation showing contours or areas of similar wavelength of maximum fluorescent intensity. Such images reveal structural weaknesses within the object being studied.

BRIEF DESCRIPTION OF THE DRAWINGS

The above and further features of the present invention may best be understood with reference to the following Detailed Description and the Figures in which:

FIG. 1 is a diagram showing the components of an imaging apparatus and the general geometry of such an apparatus;

FIG. 2 is a false color image generated using the method and apparatus described herein;

DETAILED DESCRIPTION OF A PREFERRED EMBODIMENT

Figure 3:
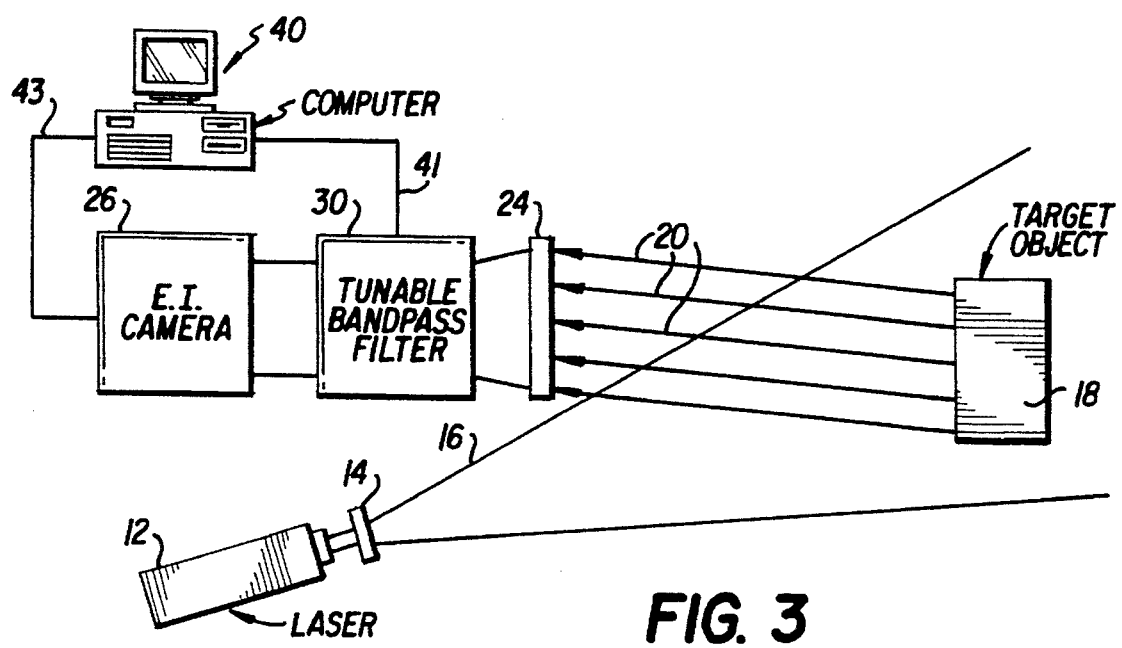
FIG. 3 is a diagram similar to FIG. 1 which shows an alternate embodiment of the apparatus of the present invention.

Referring now to the FIGURES in which like reference numerals indicate like or corresponding features throughout the views there is shown in FIG. 1 a Laser Induced Fluorescence (LIF) imaging apparatus 10 for rapidly evaluating the presence of heat damage in parts made from Polymer Matrix Composite (PMC) materials. A laser 12 was configured to shine through a lens 14 or other element to spread the beam 16 so that it evenly illuminates at least a substantial portion of the object 18 (such as an aircraft) to be analyzed.

Fluorescence 20 from the object 18 is imaged using a long pass filter 22, a collection lens 24 and an electronic imaging camera 26. (It should be noted that the fluorescence 20 shown in FIGS. 1 and 3 is a very simplified representation and that the actual fluorescence would not be collimated as it would appear to be in FIGS. 1 and 3). In a preferred embodiment, the optical filter 22 is a colored glass photography filter such as that available from Hoya. The collection lens 24 is a Nikon 50 mm focal length SLR camera lens. The camera 26 is a charge-coupled device (CCD) system from Princeton Instruments. The long pass filter 22 eliminates elastically-scattered laser radiation, making it possible to image only the fluorescence from the sample. This method allows high-resolution imaging of fluorescent intensity in between about one to ten seconds.

Referring now to FIG. 2, an image prepared using the method and apparatus just described is shown. A 12-inch square tetraglycidyl 4, $4^1$ diaminodiphenyl methane (TGDDM) epoxy resin system with a diaminodiphenyl sulfone (DDS) cure PMC panel was heated at its center to produce a damaged area approximately 4×4 inches square. In the false-colored image of FIG. 2, the damaged area is clearly apparent. The image of FIG. 2 consists of an array (approximately 300×300 points) of intensity measurements for specific points corresponding to points on the sample. Areas of corresponding intensity are assigned a color to produce an image consisting of contours of like intensity to produce the false color image of FIG. 2.

Referring now to FIG. 3, a more advanced form of the preferred embodiment is shown. Once again, a beam from a laser 12 is spread as by a lens 14 to produce a beam 16 which substantially illuminates the target object 18 with the laser radiation. The fluorescence 20 is again collected using a lens 24, but is then directed through an electronically tunable bandpass filter 30. If desired, a long-pass filter such as that identified by reference numeral 22 of FIG. 1 may also be used to block elastically scattered and collected laser radiation. After exiting the filter 30, the collected fluorescence 20 is directed to a camera 26. The tunable filter 30 (such as an acousto-optical tunable filter) allows narrow wavelength bands to be passed to the camera 26, making it possible to generate a multitude of images of the fluorescence of the object in different wavelength bands.

Figure 4:
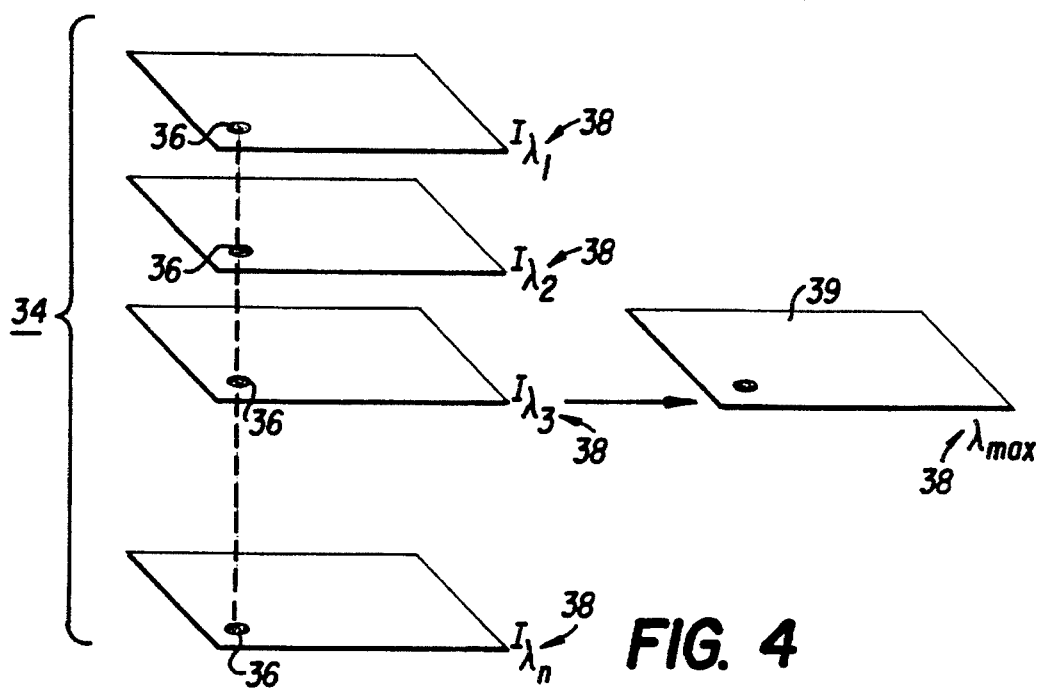
FIG. 4 is a diagram showing how an array of images is processed to generate the desired image in accordance with the present invention.

Referring now to FIG. 4, a schematic representation shows how a set of n intensity images at specific wavelengths 32 can be processed as an array of images 34 (spanning wavelengths ranging from $\lambda_1$ to $\lambda_n$). The intensity at specific points 36 in each frame of the array 34 is evaluated as a function of wavelength 32 to produce an image of fluorescence wavelength shift or maximum wavelength 38.

This image transformation provides a quantitative image of heat damage, based on the singular functional relationship between wavelength of maximum fluorescence intensity and heat damage, for example of the form:

$$\text{Heat Damage} = a_o + a_1 \lambda_{max} + a_2 (\lambda max)^2$$

where $a_o$, $a_1$, and $a_2$ are the coefficients of a second-order polynomial. Equations such as this can be used to directly transform the wavelength image into a quantitative heat damage image 39.

In this preferred embodiment, preferably the control of the tunable band-pass filter 30 is provided by a computer 40 along line 41 as is shown in FIG. 3. Similarly, the output of the CCD camera 26 is provided to the computer 40 along line 43. Thus, the entire process of generating the array of images 34 at the specific wavelengths 32 may be controlled by the computer 40. Likewise, the processing of the array 34, as received by the computer from the camera 26, into the heat damage image 39.

While preferred embodiments of the present invention were described above, this detailed description is for the purpose of illustration and not limitation. The above described embodiments are capable of numerous modifications, substitutions and deletions without departing from the scope of the claims as set forth below. For example, a variety of filters may be substituted for the long-pass and tunable bandpass filters described above. Furthermore, a variety of imaging systems could be used in place of a CCD camera system. As a further embodiment, two imaging camera systems could be located a short distance apart and operated simultaneously, and the resulting parallax in the two images used to create a three-dimensional image of the sample and its heat damage. Alternatively, one camera could be repositioned and the images collected sequentially at two positions used to achieve the same three-dimensional effect. This approach would be very useful to analyze complex surfaces such as the undercarriage structures of airplanes. Further, an image based on the elastic scatter of the laser radiation 16 could be generated (as by removing the long pass filter 22 from the optical path) to uniformly map the surface of the object 18 being studied. This image could be combined with the fluorescence image to provide a clear surface reference for features observed in the fluorescence image.

EXAMPLE I

A study was made of IM6/3501-6 laminate panel specimens having the layup [+45°, 90°, (−45°, +45°), 0°, (+45°, −45°), 90°, −45°]. Table 1 below summarizes the flexural strength, statistical variation, and conditions of oxidation from the specimens evaluated.

TABLE 1

| Time Minutes | Temperature °F. | Failure Load* | | | Standard deviation kpsi | Number of Samples |
|---|---|---|---|---|---|---|
| | | −95% kpsi | Mean kpsi | +95% kpsi | | |
| | 75 | 47.04 | 53.08 | 59.13 | 3.11 | 6 |
| 60 | 350 | 48.98 | 52.27 | 55.55 | 1.69 | 6 |
| 60 | 450 | 37.66 | 46.02 | 54.37 | 4.30 | 6 |
| 5 | 550 | 34.13 | 42.39 | 50.65 | 4.44 | 8 |
| 30 | 550 | 19.96 | 29.77 | 39.58 | 5.18 | 7 |
| 60 | 550 | 12.56 | 18.85 | 25.14 | 3.38 | 8 |
| 5 | 650 | 2.47 | 8.17 | 13.86 | 2.93 | 6 |
| 30 | 650 | 1.94 | 2.82 | 3.70 | 0.44 | 5 |
| 60 | 650 | 1.95 | 2.62 | 3.28 | 0.34 | 6 |
| 30 | 750 | 0.85 | 3.43 | 6.01 | 1.10 | 3 |

*The factor for converting kpsi to MPa is 6.894.

Above 500° F., radiant heating of the IM6/3501-6 laminate results in strength losses that occur rapidly and that are measured with reasonable accuracy. Below 500° F., strength loss occurs much slower, so that at 450° F. for 60 minutes some strength loss is measured, but at 350° F. for 60 minutes strength loss is not detected.

Experiments were conducted using laser excitation from the ultraviolet to the near infrared. Measurements were made of spectral response at wavelengths ranging from the laser line up to the upper limit of emission, generally 300–400 nm above the excitation wavelength. The extent of fluorescence bandwidth is indicative of the large, highly conjugated nature of the polymerized resin. The study examined both peak fluorescence intensity and wavelength of peak fluorescence, using laser excitation ranging from 325 to 785-nm (helium cadmium, helium neon, argon- and krypton-ion, and GaAs semiconductor lasers were used). Characterization of fluorescence emission was achieved using a 270-mm focal length, f/4 imaging spectrograph (270M, Spex Industries) coupled with a cryogenically cooled CCD array detector (LN/CCD-500B, Princeton Instruments). A 10× microscope objective was used for both excitation and collection of fluorescence from a 100-nm diameter portion of the surface of the panel being examined. Long pass colored glass (manufactured by Schott or Hoya) or holographic (manufactured by Kaiser) filters were used at each laser wavelength to reject elastically scattered laser light. The filters allowed fluorescent wavelengths starting at approximately 10 to 15 nm above the laser line and extending beyond 900 nm to be examined. Data collected for each panel allowed peak fluorescence intensity and wavelength to be determined.

Figure 5:
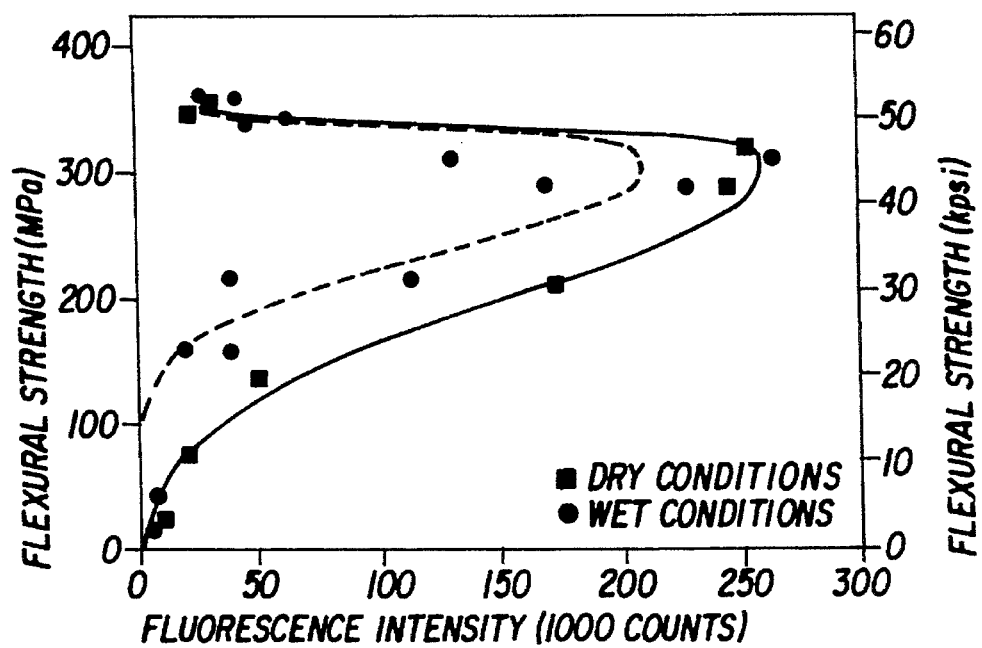
FIG. 5 is a graph showing the dependency of fluorescence intensity of an object to the flexural strength of the object; and, FIG. 6 is a graph showing the relationship between maximum fluorescence wavelength and flexural strength.
Figure 6:
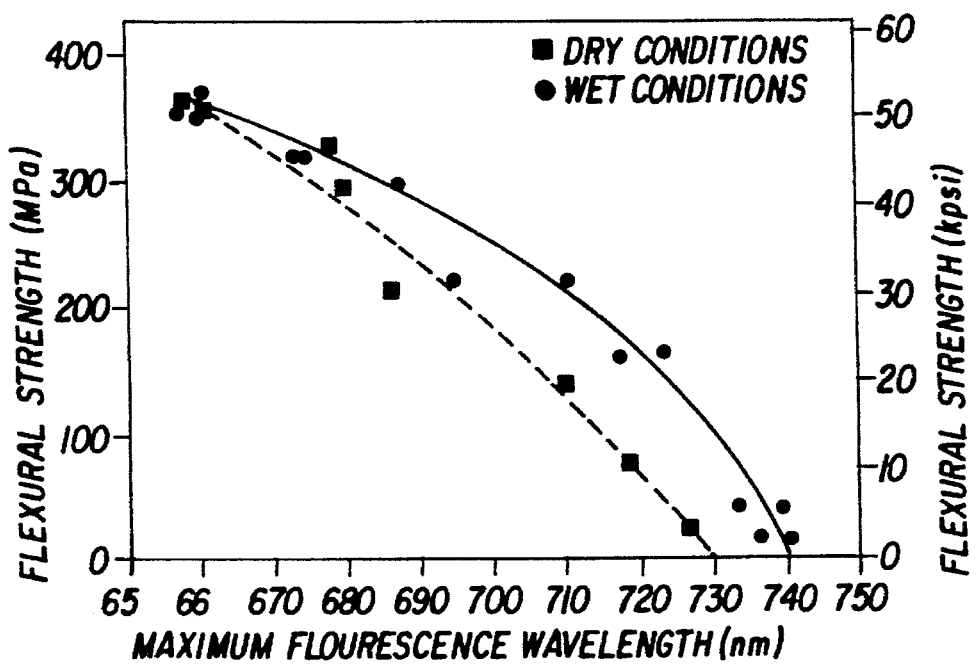

The specimens used in our experiments were typically in sets of two wet and one dry exposed specimens from the oxidation exposure sequence listing in Table 1. For each excitation wavelength, peak fluorescent intensity and wavelength of peak intensity were compared with measured strength properties for each specimen. Greatest correlation was observed using helium neon laser excitation at 633 nm. FIG. 5 shows the fluorescence intensity as a function of flexural strength for specimens that were exposed to wet or dry conditions prior to oxidation. FIG. 5 further shows that the fluorescence intensity increases with early stages of oxidation at levels that affect strength, then decays with further oxidative strength loss. FIG. 6 shows that the wavelength of peak fluorescence intensity shifts to the red with extent of oxidation and this shift correlated in a singular functional respect with flexural strength.

These experiments also detected fluorescence from small particulates (about 5 μm) of unreacted hardener (DDS) that give high fluorescence yields. Evaluation of several sources of IM6/3501-6 indicated that this was not a unique occurrence and care must be taken to exclude such fluorescence from the measurement.

As a result of the experiments, it has been determined that the optimal excitation laser is a 633 nm helium neon laser. This wavelength not only had the best correlation to flexural strength measurements in samples, but also minimized the contribution to fluorescence from the unreacted particulates. Further, excitation at longer wavelengths results in missing fluorescence emissions in the 650–670 nm range which are characteristic of mildly heat damaged PMC's.

We claim:

1. A method for detecting structural weakness in Polymer Matrix Composite (PMC) items comprising the steps of:
   generating a beam of laser light;
   illuminating the PMC item with the beam of laser light;
   collecting fluorescence emitted by the PMC item;
   imaging the collected fluorescence; and
   analyzing said imaged fluorescence to detect areas of structural weakness in the PMC item.

2. A method as described by claim 1 wherein said analysis comprises correlation of emitted fluorescence wavelength to a corresponding fluorescence intensity.

3. A method as described by claim 2 wherein said analysis comprises correlation of a plurality of emitted fluorescence wavelengths to corresponding fluorescence intensities.

4. A method as described by claim 3 wherein said plurality of emitted fluorescence wavelengths are correlated to corresponding fluorescence intensities by the approximate relation of $a_o + a_1 \lambda max + a_2 (\lambda max)^2$ where $a_o$, $a_1$ and $a_2$ are coefficients of a second order polynomial and $\lambda$ max is the fluorescence wavelength of maximum fluorescence intensity.

5. A method as described by claim 1 wherein said beam of laser light has a wavelength within the range of about 325 nm to about 785 nm.

6. A method as described by claim 3 wherein said correlation comprises a composite image that displays a representation of fluorescence wavelengths of maximum fluorescence intensities respective to discreet area increments of a tested PMC item.

7. A method as described by claim 6 wherein said correlation comprises a false color image representing an assignment of fluorescence wavelength of maximum fluorescence intensity to discreet area increments of a tested PMC item.

8. The method of claim 1 wherein the step of collecting fluorescence emitted by the PMC item includes the further steps of:
   processing said collected fluorescence through a tunable bandpass filter;
   selectively and sequentially tuning said filter through a range of discreet wavelengths;
   determining the intensity of the collected fluorescence at each of said discreet wavelengths at a plurality of points in the collected fluorescence corresponding to locations on the PMC item; and
   wherein said step of imaging said collected fluorescence further includes displaying the image of the PMC item as a function of the wavelength of maximum intensity at each of said plurality of points.

9. The method of claim 8 wherein said step of imaging said collected fluorescence further includes displaying discreet area increments of a tested PMC item as a false color image.

10. An apparatus for optically determining the presence of structural weaknesses in a Polymer Matrix Composite (PMC) item comprising:
    a laser generating a laser beam;
    directional optics means for directing and dispersing said laser beam to illuminate the PMC item;
    collection optics means for collecting and directing fluorescence emitted by the PMC item;
    display means for displaying the collected fluorescence so that structural weakness in the PMC item may be detected.

11. An apparatus as described by claim 10 wherein said laser beam has a wavelength within the range of about 325 nm to about 785 nm.

12. An apparatus as described by claim 11 wherein said display means comprises a false color image display to represent an assignment of fluorescence wavelengths of maximum fluorescence intensity to discreet area increments of a tested PMC item.

* * * * *